(12) United States Patent
Bräunlich et al.

(10) Patent No.: US 6,610,687 B1
(45) Date of Patent: Aug. 26, 2003

(54) BENZOFURANYLSULFONATES

(75) Inventors: Gabriele Bräunlich, Wuppertal (DE); Mazen Es-Sayed, Langenfeld (DE); Rüdiger Fischer, Pulheim (DE); Burkhard Fugmann, Ratingen (DE); Rolf Henning, Wuppertal (DE); Stephan Schneider, Wuppertal (DE); Michael Sperzel, Wuppertal (DE); Karl-Heinz Schlemmer, Wuppertal (DE); Graham Sturton, Maidenhead (GB); Mary F. Fitzgerald, Yarnton (GB); Barbara Briggs, Kingston (GB); Arnel Concepcion, Nara (JP); William Bullock, Easton, CT (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/979,371

(22) PCT Filed: Apr. 5, 2000

(86) PCT No.: PCT/EP00/04010
§ 371 (c)(1),
(2), (4) Date: Feb. 25, 2002

(87) PCT Pub. No.: WO00/69842
PCT Pub. Date: Nov. 23, 2000

(30) Foreign Application Priority Data

May 17, 1999 (GB) ............................................. 9911452

(51) Int. Cl.$^7$ .......................................... A61K 31/535
(52) U.S. Cl. ................... 514/233.5; 514/299; 514/333; 514/336; 514/369; 514/380; 514/397; 514/407; 514/414; 514/470; 544/153; 546/172; 546/256; 546/275.1; 546/280.4; 546/284.1; 548/185; 548/243; 548/311.4; 548/364.4; 548/454
(58) Field of Search .......................... 544/153; 546/172, 546/256, 275.1, 280.4, 284.1; 548/185, 243, 311.4, 364.4, 454; 514/233.5, 299, 333, 336, 369, 380, 397, 407, 414, 470

(56) References Cited

U.S. PATENT DOCUMENTS 5,922,740 A * 7/1999 Braunlich et al. .......... 514/337

FOREIGN PATENT DOCUMENTS

| EP | 0146243 | 6/1985 |
| EP | 0623607 | 11/1994 |
| EP | 0685479 | 12/1995 |
| EP | 0731099 | 9/1996 |
| EP | 0779291 | 6/1997 |
| WO | 9802440 | 1/1998 |

* cited by examiner

*Primary Examiner*—Fiona T. Powers

(57) ABSTRACT

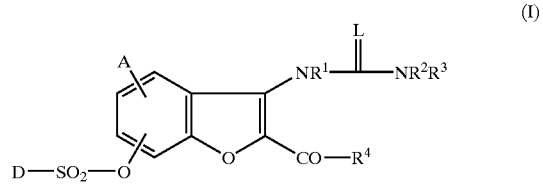

The invention relates to benzofuranylsulfonates of the general formula (I), their preparation and their use for the treatment of inflammation.

9 Claims, No Drawings

BENZOFURANYLSULFONATES

The invention relates to Benzofuranylsulfonates, processes for their preparation and their use in medicaments.

It is known that the NADPH oxidase of phagocytes is the physiological source to the superoxide radical anion and reactive oxygen species derived therefrom which are important in the defence against pathogens. Moreover, both inflammatory (e.g. TNFα, IL-1 or IL-6) and anti-inflammatory cytokines (e.g. IL-10) play a pivotal role in host defence mechanism. Uncontrolled production of inflammatory mediators can lead to acute or chronic inflammation, auto immune diseases, tissue damage, multi-organ failure and to death. It is additionally known that elevation of phagocyte cyclic AMP leads to inhibition of oxygen radical production and that this cell function is more sensitive than others such as aggregation or enzyme release.

Benzofuran derivatives having phosphodiesterase IV (PDE IV)-inhibiting action are described in the publication EP 731 099. The reference describes only one methane-sulfonic acid ester, however.

In order to provide alternative compounds of similar or improved PDE IV-inhibitory activity, the present invention relates to Benzofuranylsulfonates of the general formula

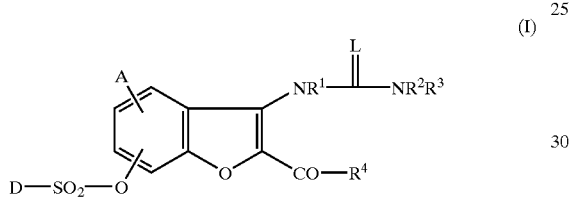

(I)

in which
A represents hydrogen, straight-chain or branched acyl or alkoxycarbonyl, each having up to 6 carbon atoms, halogen, carboxyl, cyano, nitro, hydroxyl, trifluoromethyl or trifluoromethoxy, or straight-chain or branched alkyl having up to 6 carbon atoms, which is optionally substituted by carboxyl, alkoxy or alkoxycarbonyl each having up to 4 carbon atoms, phenoxy or benzoyl, $R^1$ represents hydrogen, straight-chain or branched alkyl having up to 4 carbon atoms, an amino protecting group or a group of the formula —CO—$R^5$ in which
$R^5$ denotes straight chain or branched alkoxy having up to 4 carbon atoms, $R^2$ and $R^3$ are identical or different and represent hydrogen, cycloalkyl having up to 6 carbon atoms, straight chain or branched alkyl, alkoxycarbonyl or alkenyl each having up to 8 carbon atoms, or $R^2$ and $R^3$ together with the nitrogen atom form a 5- to 7-membered saturated heterocycle optionally having a further O atom, $R^4$ represents aryl having 6 to 10 carbon atoms or represents a 5 to 7 membered, aromatic, saturated or unsaturated heterocycle, which can contain up to 3 oxygen, sulphur and/or nitrogen atoms as hetero-atoms or a residue of a formula —NR$^6$, wherein
$R^6$ denotes hydrogen or straight-chain or branched alkyl or alkoxycarbonyl each having up to 6 carbon atoms,
and to which further a benzene ring can be fused and wherein aryl and/or the heterocycle are optionally monosubstituted to trisubstituted by identical or different substituents from the series comprising hydroxyl, halogen, nitro, 1H-tetrazolyl, pyridyl, trifluoromethyl, trifluoromethoxy, difluoromethyl, difluoromethoxy, cyano, carboxy, straight-chain or branched alkoxy, alkoxycarbonyl or acyl each having up to 6 carbon atoms or by straight-chain or branched alkyl having up to 5 carbon atoms, which is optionally substituted by carboxyl or straight-chain or branched alkoxycarbonyl having up to 4 carbon atoms or by a group of formula —NR$^7$R$^8$, —SR$^9$, —(NH)$_a$—SO$_2$R$^{10}$ or —O—SO$_2$R$^{11}$, in which
$R^7$ and $R^8$ are identical or different and denote hydrogen or a straight-chain or branched alkyl having up to 4 carbon atoms, or
$R^7$ denotes hydrogen
and
$R^8$ denotes straight-chain or branched acyl having up to 6 carbon atoms $R^9$ denotes hydrogen or straight-chain or branched alkyl having up to 4 carbon atoms, a denotes a number 0 or 1, $R^{10}$ and $R^{11}$ are identical or different and represent straight-chain or branched alkyl having up to 6 carbon atoms, benzyl or phenyl, which are optionally substituted by trifluoromethyl, halogen or straight-chain or branched alkyl having up to 4 carbon atoms, L represents an oxygen or sulfur atom, D represents a residue of a formula

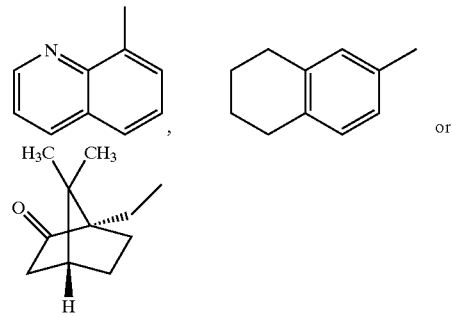

or aryl having 6 to 10 carbon atoms or a 5 to 7-membered aromatic, saturated or unsaturated heterocycle having up to 3 heteroatoms from the series comprising N, S and O and to which a phenyl ring can be fused, wherein all abovementioned residues and ring systems are optionally monosubstituted to trisubstituted by halogen, carboxyl, straight-chain or branched alkyl or alkoxycarbonyl each having up to 6 carbon atoms, pyridyl and/or by a residue of a formula —NR$^{12}$—E—R$^{13}$, —NR$^{14}$—CO—NR$^{15}$R$^{16}$, —NR$^{17}$—SO$_2$—NR$^{18}$R$^{19}$, —SO$_2$—R$^{20}$ or —(SO$_2$)$_b$—$_{NR}$$^{21}$R$^{22}$, wherein
b denotes a number 0 or 1,
E denotes a residue of formula SO$_2$ or CO
$R^{12}$, $R^{14}$, $R^{15}$, $R^{16}$, $R^{17}$, $R^{18}$, $R^{19}$, $R^{21}$ and $R^{22}$ are identical or different and denote hydrogen, phenyl or straight-chain or branched alkyl having up to 6 carbon atoms, $R^{13}$ denotes straight-chain or branched alkyl or alkoxy each having up to 6 carbon atoms, $R^{20}$ denotes benzyl, phenyl, pyridyl or straight-chain or branched alkyl having up to 6 carbon atoms, or D represents straight-chain or branched alkyl or alkenylen having up to 8 carbon atoms, which are monosubstituted to trisubstituted by halogen, aryl having 6 to 10 carbon atoms or a 5 to 7-membered saturated or unsaturated heterocycle having up to 3 heteroatoms from the series comprising N, S and O and to which a phenyl ring can be fused or by a residue of a formula —$NR^{23}R^{24}$ or wherein
$R^{23}$ and $R^{24}$ have the abovementioned meaning of $R^{15}$ and $R^{16}$ and are identical or different to the latter, wherein the abovementioned ring systems are optionally substituted by halogen, and in the case that $R^4$ does not represent phenyl or substituted phenyl, D in addition can represent benzyl or straight-chain or branched alkyl having up to 5 carbon atoms, or D optionally represents a residue of a formula —$NR^{25}R^{26}$
wherein
$R^{25}$ and $R^{26}$ have the abovementioned meaning of $R^{21}$ and $R^{22}$ and are identical or different to the latter, and salts thereof.

The benzofuranylsulfonates according to the invention can also be present in the form of their salts. In general, salts with organic or inorganic bases or acids may be mentioned here.

Physiologically acceptable salts are preferred in the context of the present invention. Physiologically acceptable salts of the Benzofuranylsulfonates can be metal or ammonium salts of the substances according to the invention, which contain a free carboxylic group. Those which are particularly preferred are, for example, sodium, potassium, magnesium or calcium salts, and also ammonium salts which are derived from ammonia, or organic amines, such as, for example, ethylamine, di- or triethylamine, di- or triethanolamine, dicyclohexylamine, dimethylaminoethanol, arginine, lysine or ethylenediamine.

Physiologically acceptable salts can also be salts of the compounds according to the invention with inorganic or organic acids. Preferred salts here are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric, acid, tartaric acid, ethanesulphonic acid, benzenesulphonic acid, toluenesulphonic acid or naphthalenedisulphonic acid.

The compounds according to the invention can exist in stereoisomeric forms which either behave as image and mirror image (enantiomers), or which do not behave as image and mirror image (diastereomers). The invention relates both to the antipodes and to the racemate forms, as well as to individual diastereomers and to the diastereomer mixtures. The racemate forms, like the diastereomers, can be separated into the stereoisomerically uniform constituents in a known manner.

Heterocycle in general represents a 5- to 7-membered, aromatic, saturated or unsaturated, preferably 5- to 6-membered, aromatic, saturated or unsaturated ring which can contain up to 3 oxygen, sulphur and/or nitrogen atoms as heteroatoms and to which further aromatic rings can be fused.

The following are mentioned as preferred: thienyl, furyl, pyrrolyl, pyridyl, pyrimidyl, pyrazinyl, pyridazinyl, quinolyl, isoquinolyl, quinazolyl, quinoxazolyl, thiazolyl, dihydrothiazolyl, benzothiaazolyl, isothiazolyl, benzisothiazolyl, oxazolyl, benzoxazolyl, isoxazolyl, imidazolyl, benzimidazolyl, indolyl, morpholinyl pyrrolidinyl, piperidyl, piperazinyl, oxazolinyl or triazolyl.

Preferred compounds of the general formula (I) are those in which

A represents hydrogen, halogen, carboxyl, cyano, nitro, hydroxyl, trifluoromethyl, trifluoromethoxy or alkoxy having up to 4 carbon atoms $R^1$ represents hydrogen, straight-chain or branched alkyl having up to 4 carbon atoms or a group of the formula —O—$R^5$
in which
$R^5$ denotes straight chain or branched alkoxy having up to 4 carbon atoms, $R^2$ and $R^3$ are identical or different and represent hydrogen, cyclobutyl, cyclopentyl, cyclohexyl or straight-chain or branched alkyl, alkoxycarbonyl or alkenyl each having up to 4 carbon atoms, or or $R^2$ and $R^3$ together with the nitrogen atom form a pyrrolidinyl-, piperidinyl- or morpholinyl-ring, and $R^4$ represents phenyl, pyridyl or thienyl, wherein all rings are optionally monosubstituted to trisubstituted by identical or different substituents from the series comprising hydroxyl, fluorine, chlorine, bromine, nitro, carboxy, straight-chain or branched alkoxy, alkoxycarbonyl or acyl each having up to 3 carbon atoms, or by straight-chain or branched alkyl having up to 3 carbon atoms, which is optionally substituted by carboxyl or straight-chain or branched alkoxycarbonyl having up to 3 carbon atoms L represents an oxygen or sulfur atom, D represents a residue of a formula or phenyl, pyridyl, thienyl, furyl, pyrazolyl, oxazolyl, isoxazolyl, thiazolyl, imidazolyl, morpholinyl, piperidinyl, pyrrolidinyl or piperazinyl, wherein all abovementioned residues and ring systems are optionally monosubstituted to trisubstituted by halogen, carboxyl, straight-chain or branched alkyl or alkoxycarbonyl each having up to 4 carbon atoms, pyridyl and/or by a residue of a formula —NR$^{12}$E—R$^{13}$, —NR$^{14}$—CO—NR$^{15}$R$^{16}$, —NR$^{17}$—SO$_2$—NR$^{18}$R$^{19}$, —SO$_2$—R$^{20}$ or —(SO$_2$)$_b$—NR$^{21}$R$^{22}$,
wherein
b denotes a number 0 or 1,
E denotes a residue of formula SO$_2$ or CO
R$^{12}$, R$^{14}$, R$^{15}$, R$^{16}$, R$^{17}$, R$^{18}$, R$^{19}$, R$^{21}$ and R$^{22}$ are identical or different and denote hydrogen, phenyl or straight-chain or branched alkyl having up to 4 carbon atoms,
R$^{13}$ denotes straight-chain or branched alkyl or alkoxy each having up to 4 carbon atoms,
R$^{20}$ denotes benzyl, phenyl, pyridyl, ethyl or methyl, or D represents straight-chain or branched alkyl or alkenylen having up to 6 carbon atoms, which are monosubstituted to trisubstituted by halogen, phenyl, pyridyl, thienyl, furyl, imidazolyl, morpholinyl, piperidinyl, pyrrolidinyl, piperazinyl or by a residue of a formula —NR$^{23}$R$^{24}$ or

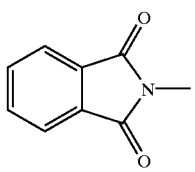

wherein
R$^{23}$ and R$^{24}$ have the abovementioned meaning of R$^{15}$ and R$^{16}$ and are identical or different to the latter,
wherein the abovementioned ring systems are optionally substituted by halogen,
and in the case that
R$^4$ does not represent phenyl or substituted phenyl,
D in addition can represent benzyl or straight-chain or branched alkyl having up to 4 carbon atoms, or D optionally represents a residue of a formula —NR$^{25}$R$^{26}$
wherein
R$^{25}$ and R$^{26}$ have the abovementioned meaning of R$^{21}$ and R$^{22}$ and are identical or different to the latter,
and salts thereof.

Particularly preferred compounds of the general formula (I) are those
in which
A, R$^2$ and R$^3$ represent hydrogen, R$^1$ represents hydrogen or straight-chain or branched alkyl having up to 3 carbon atoms or a group of the formula —CO—R$^5$,
in which
R$^5$ denotes straight chain or branched alkoxy having up to 3 carbon atoms,
R$^4$ represents phenyl or pyridyl, which are optionally up to difold substituted by identical or different substituents from the series fluorine, chlorine, methyl or methoxy,
L represents an oxygen atom, D represents a residue of a formula

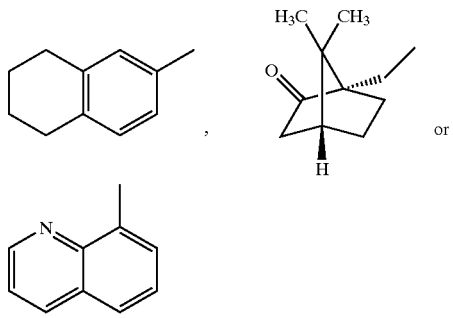

or phenyl, pyridyl, thienyl, pyrazolyl, oxazolyl, isoxazolyl, thiazolyl, imidazolyl, morpholinyl, piperidinyl, pyrrolidinyl or piperazinyl, wherein all abovementioned residues and ring systems are optionally monosubstituted to trisubstituted by halogen, carboxyl, straight-chain or branched alkyl or alkoxycarbonyl each having up to 3 carbon atoms, pyridyl and/or by a residue of a formula —NR$^{12}$—E—R$^{13}$, —NR$^{14}$—CO—NR$^{15}$R$^{16}$, —NR$^{17}$—SO$_2$—NR$^{18}$R$^{19}$, —SO$_2$—NR$^{18}$R$^{19}$, —SO$_2$—R$^{20}$ or —SO$_2$)$_b$—NR$^{21}$R$^{22}$,
wherein
b denotes a number 0 or 1,
E denotes a residue of formula SO$_2$ or CO
R$^{12}$, R$^{14}$, R$^{15}$, R$^{16}$, R$^{17}$, R$^{18}$, R$^{19}$, R$^{21}$ and R$^{22}$ are identical or different and denote hydrogen, phenyl or straight-chain or branched alkyl having up to 3 carbon atoms,
R$^{13}$ denotes straight-chain or branched alkyl or alkoxy each having up to 3 carbon atoms,
R$^{20}$ denotes benzyl, phenyl or methyl, or D represents straight-chain or branched alkyl or alkenylen having up to 4 carbon atoms, which are monosubstituted to trisubstituted by halogen, phenyl, pyridyl, thienyl, furyl, imidazolyl, morpholinyl, piperidinyl, pyrrolidinyl, piperazinyl or by a residue of a formula —NR$^{23}$R$^{24}$ or

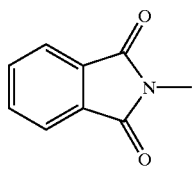

wherein
R$^{23}$ and R$^{24}$ have the abovementioned meaning of R$^{15}$ and R$^{16}$ and are identical or different to the latter,
wherein the abovementioned ring systems are optionally substituted by halogen,
and in the case that
R$^4$ does not represent phenyl or substituted phenyl,
D in addition can represent benzyl or straight-chain or branched alkyl having up to 3 carbon atoms, or D optionally represents a residue of a formula —NR$^{25}$R$^{26}$
wherein
R$^{25}$ and R$^{26}$ have the abovementioned meaning of R$^{21}$ and R$^{22}$ and are identical or different to the latter
and salts thereof.

A process for the preparation of the compounds of the general formula (I) has additionally been found, characterized in that
compounds of the general formula (II)

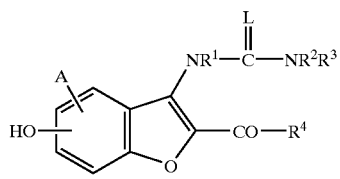

in which
A, L, $R^1$, $R^2$, $R^3$ and $R^4$ have the abovementioned meaning
are reacted with compounds of the general formula (III)

in which
D has the abovementioned meaning,
in inert solvents, if appropriate in the presence of a base and/or in the presence of an auxiliary.

The process according to the invention can be illustrated by way of example by the following equation:

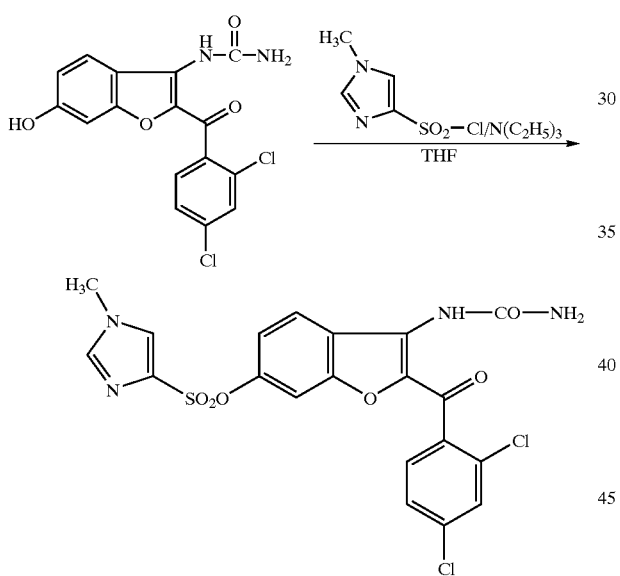

Suitable solvents are generally customary organic solvents which do not change under the reaction conditions. These include ethers such as diethyl ether, dioxane or tetrahydrofurane. Tetrahydrofurane is preferred.

Suitable bases and auxiliaries are generally organic bases. Organic amines (trialkyl-($C_1$–$C_6$)amines) such as triethylamine, or heterocycles such as 1,4diazabicyclo-[2.2.2]octane (DABCO), 1,8-diazabicyclo[5.4.0]undec-7-ene (DBU) or 4-dimethylaminopyridine. Triethylamine and 4-dimethylaminopyridine are preferred.

The base is employed in an amount from 1 mol to 10 mol, preferably from 1.0 mol to 4 mol, relative to 1 mol of the compounds of the general formula (III).

In case 4-dimethylaminopyridine is employed, the base is used in a catalytic amount.

The auxiliary is employed in an amount from 1 mol to 10 mol, preferably from 1.0 mol to 4 mol, relative to 1 mol of the compounds of the general formula (III).

The process is in general carried out in a temperature range from −30° C. to +30° C., preferably from −10° C. to +20° C.

The process is generally carried out at normal pressure. However, it is also possible to carry it out at elevated pressure or at reduced pressure (for example in a range from 0.5 to 5 bar).

The compounds of the general formula (II) are known or as species new and can be prepared characterized in that

[A] first compounds of the general formula (IV)

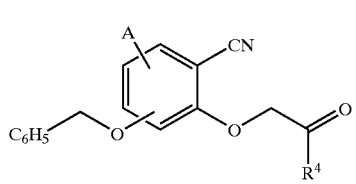

in which
A and $R^4$ have the abovementioned meaning,
are reacted with a catalytic amount of base, such as alkali alcoholates, preferred sodium ethanolate to compounds of the general formula (V)

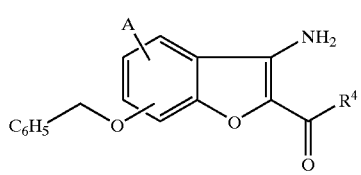

in which
A and $R^4$ have the abovementioned meaning,
followed by reaction with compounds of the general formula (VI)

in which
$R^2$ has the abovementioned meaning,
in inert solvents, if appropriate in the presence of a base and/or in the presence of an auxiliary to compounds of a general formula (VII)

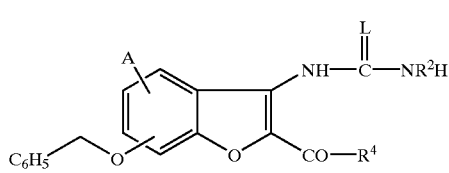

in which
A, L, $R^2$ und $R^4$ have the abovementioned meaning,
and in a last step the benzyl group is removed by hydrogenation,
or

[B] compounds of the general formula (VIII)

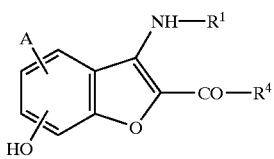
(VIII)

in which

A, $R^1$ and $R^4$ have the abovementioned meaning
are reacted with compounds of the, general formula (I)

$R^2$—N=C=L  (VI)

in which

L and $R^2$ have the abovementioned meaning,
in inert solvents, if appropriate in the presence of a base
and in the case of $R^2/R^3$=H and L=O,
compounds of the general formula (V) or (VIII) are reacted with compounds of the general formula (IX)

E—$SO_2$—N=C=O  (IX)

in which

E denotes halogen, preferably chlorine,
and in the case of $R^2/R^3$=H and L=S,
compounds of the general formula (V) or (VIII) are reacted with $NH_4SCN$, and in case of $R^1$, $R^2$ and/or $R^3 \neq H$ the free amino groups are derivated optionally by common methods.

Suitable solvents for the first step of the procedure [A] (IV–V) are generally alcohols such as methanol, ethanol or propanol. Ethanol is preferred.

Suitable bases for the first step are general bases, such as alkali alcoholates, e.g. sodium methanolate, sodium ethanolate or sodium propanolate. Sodium ethanolate ist preferred.

The base is employed in catalytic amounts.

The process is in general carried out in a temperature range from 0° C. to 60° C., preferably at room temperature.

The process is generally carried out at normal pressure. However, it is also possible to carry out it at elevated pressure or at reduced pressure (for example in a range from 0.5 to 5 bar).

Suitable solvents for the second step of the procedure [A] (V–VII) are generally customary organic solvents which do not change under the reaction conditions. These include ethers such as diethyl ether, dioxane or tetrahydrofurane, dimethylsulfoxide, dimethylformamide, halogenohydrocarbons such as dichloromethane, trichloromethane or tetrachloromethane. Dichloromethane is preferred.

The process is in general carried out in a temperature range from –30° C. to +40° C., preferably from –10° C. to room temperature.

The process is generally carried out at normal pressure. However, it is also possible to carry out it at elevated pressure or at reduced pressure (for example in a range from 0.5 to 5 bar).

The hydroxyl-protective group is in general removed with hydrogen in ethylacetate, diethyl ether or tetrahydrofuran. Suitable catalysts- are noble metal catalysts, preferably palladium and palladium on charcoal.

Suitable solvents for the procedure [B] are generally customary organic solvents which do not change under the reaction conditions. These include ethers such as diethyl ether, dioxane or tetrahydrofurane, dimethylsulfoxide, dimethylformamide or halogenohydrocarbons such as dichloromethane, trichloromethane or tetrachloromethane. Dichloromethane is preferred.

The process, is in general carried out in a temperature range from –30° C. to +100° C., preferably from –10° C. to +50° C.

The process is generally carried out at normal pressure. However, it is also possible to carry out it at elevated pressure or at reduced pressure (for example in a range from 0.5 to 5 bar).

The compounds of the general formula (IV) are as species new and can be prepared by reaction of compounds of the general formula (X)

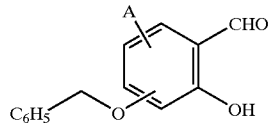
(X)

in which

A has the abovementioned meaning,
with hydroxylamine hydrochloride in a presence of sodium formiate to compounds of the general formula (XI)

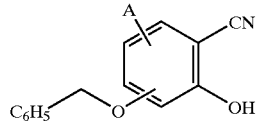
(XI)

in which

A has the abovementioned meaning,
followed by reaction with compounds of the general formula (XII)

$R^4$—CO—$CH_2$—T  (XII)

in which $R^4$ has the abovementioned meaning,
and

T represents halogen, preferably bromine,
in inert solvents and in the presence of a base.

Suitable solvents are generally customary organic solvents which do not change under the reaction conditions. These include ethers such as diethyl ether, dioxane or tetrahydrofuran, acetone, dimethylsulfoxide, dimethylformamide or alcohols such as methanol, ethanol, propanol or halogenohydrocarbons such as dichloromethane, trichloromethane or tetrachloromethane. Acetone and dimethylformamide are preferred.

Suitable bases for the procedure are generally inorganic or organic bases. These preferably include alkali metal hydroxides such as, for example; sodium hydroxide or potassium hydroxide, alkaline earth metal hydroxides such as, for example, barium hydroxide, alkali metal carbonates such as sodium carbonate, potassium carbonate, alkaline earth metal carbonates such as calcium carbonate. Potassium carbonate (powdered) is preferred.

The base is employed in an amount from 1 mol to 10 mol, preferably from 1.0 mol to 4 mol, relative to 1 mol of the compounds of the general formulae (XI).

The process is in general carried out in a temperature range from –30° C. to +100° C. preferably from –10° C. to +60° C.

The process is generally carried out at normal pressure. However, it is also possible to carry out it at elevated pressure or at reduced pressure (for example in a range from 0.5 to 5 bar).

The compounds of the general formula (X) are known or as species new and be can prepared by reaction of 2,4-dihydroxy-benzaldehydes with benzylbromide in one of the abovementioned solvents and bases, preferably in acetone with potassium carbonate at room temperature.

The compounds of the general- formulae (II), (IV), (VII), (IX) and (XII) are as species new and can be prepared like described above.

The compounds of the general formulae (III), (VI), (VIII), (IX) and (XII) are known or as species new and can be prepared by customary methods.

The compounds of the general formula (V) can be prepared like described above or in a single step procedure by reacting compounds of the general formula (XI) with compounds of the general formula (XII) in the presence of a surplus of sodium ethylate under reflux.

Surprisingly it was found that compounds given by the general formula (I) inhibited oxygen radical formation as well as TNFα (tumor necrosis factor) production, but potentiated the release of IL-10. These compounds elevated cellular cyclic AMP probably by inhibition of phagocyte phosphodiesterase activity.

The compounds according to the invention specifically inhibit the production of super-oxide by polymorphonuclear leukocytes (PMN). Furthermore, these compounds inhibit TNFα release and potentiate IL-10 production in human monocytes in response to a variety of stimuli including bacterial lipopolysaccharide (LPS), complement-opsonized zymosan (ZymC3b) and IL-1β.

The described effects are probably mediated by the elevation of cellular cAMP probably due to inhibition of the type IV phosphodiesterase responsible for its degradation.

They can therefore be employed in medicaments for the treatment of acute and chronic inflammatory processes.

The compounds according to the invention are preferably suitable for the treatment and prevention of acute and chronic inflammation and auto immune diseases, such as emphysema, alveolitis, shock lung, all kinds of asthma, COPD, ARDS, bronchitis, arteriosclerosis, arthrosis, inflammations of the gastrointestinal tract, rheumatoid arthritis, myocarditis, sepsis and septic shock, arthritis, rheumatoid spondylitis and osteoarthritis, gram negative sepsis, toxic shock syndrome, acute respiratory distress syndrome, bone resorption diseases, reperfusion injury, graft vs host reaction, allogroft rejection, malaria, myalgias, HIV, AIDS, cachexia, Crohn's disease, ulcerative colitis, pyresis, system lupus erythematosus, multiple sclerosis, type I diabetes mellitus, psoriasis, Bechet's disease, anaphylactoid purpura nephritis, chronic glomerulonephtritis, inflammatory bowel disease and leukemia. The compounds according to the invention are additionally suitable for reducing the damage to infarct tissue after reoxygenation. In this case the simultaneous administration of allopurinol to inhibit xanthine oxidase is of advantage. Combination therapy with superoxide dismutase is also of use.

Test description

1. Preparation of Human PMN

Blood was taken from healthy subjects by venous puncture and neutrophils were purified by dextran sedimentation and resuspended in the buffered medium.

2. Inhibition of FMLP-stimulated Production of Superoxide Racidal Anions.

Neutrophils ($2.5 \times 10^5$ ml$^{-1}$) were mixed with cytochrome C (1.2 mg/ml) in the wells of a microtitre plate. Compounds according to the invention were added in dimethyl sulphoxide (DMSO). Compound concentration ranged from 2.5 nM to 10 µM, the DMSO concentration was 0.1% v/v in all wells. After addition of cytochalasin b (5 µg×ml$^{-1}$) the plate was incubated for 5 min at 37° C. Neutrophils were then stimulated by addition of $4 \times 10^{-8}$ M FMLP and superoxide generation measured as superoxide dismutase inhibitable reduction of cytochrome C by monitoring the OD$_{550}$ in a microtitre plate spectrophotometer, e.g. a thermomax microtitre plate spectrophotometer. Initial rates were calculated using a kinetic calculation programme such as a softmax programme. Blank wells contained 200 units of superoxide dismutase.

The inhibition of superoxide production was calculated as follows:

$$\frac{[1 - ((Rx - Rb))]}{((Ro - Rb))} \cdot 100 = \% \text{ inhibition}$$

Rx=Rate of the well containing the compound according to the invention.

Ro=Rate in the control well.

Rb=Rate in the superoxide dismutase containing blank well.

Compounds according to the invention have IC$_{50}$ values in the range 0.001 µM–1 µM (see Table A).

3. Measurement of PMN Cyclic AMP Concentration

The compounds according to the invention were incubated with $3.7 \times 10^6$ PMN for 5 min at 37° C. before addition of $4 \times 10^{-8}$ M FMLP. After 6 min protein was precipitated by the addition of 1% v/v conc. HCl in 96% v/v ethanol containing 0.1 mM EDTA. After centrifugation the ethanolic extracts were evaporated to dryness under N$_2$ and resuspended in 50 mM Tris/HCl pH 7.4 containing 4 mM EDTA. The cyclic AMP concentration in the extracts was determined using a cyclic AMP binding protein assay supplied by Amersham International plc. Cyclic AMP concentrations were expressed as percentage of vehicle containing control incubations.

Compounds elavate the cAMP-level at 1 µM compound 0–400% of control values.

4. Assay of PMN Phosphodiesterase

This was performed as a particulate fraction from human PMN essentially as described by Souness and Scott (Biochem. J. 291, 389–395, 1993). Particulate fractions were treated with sodium vanadate/glutathione as described by the authors to express the descrete stereospecific site on the phosphodiesterase enzyme. Compounds according to the invention had IC$_{50}$ values ranging from 0.001 µM to 1 µM (see Table A).

5. Assay of Human Platelet Phosphodiesterase

This was performed essentially as described by Schmidt et al. (Biochem. Pharmacol. 42, 153–162, 1991) except that the homogenate was treated with vanadate glutathione as above. Compounds according to the invention had IC$_{50}$ values greater than 100 µM.

6. Assay of Binding to the Rolipram Binding Site in Rat Brain Membranes

This was performed essentially as described by Schneider et al. (Eur. J. Pharmacol. 127, 105–115, 1986). Compounds according to the invention had IC$_{50}$ values in the range 0.01 to 10 µM.

7. Preparation of Human Monocytes

Blood was taken from normal donors. Monocytes were isolated from peripheral blood by density centrifugation, followed by centrifugal elutriation.

8. Endotoxin Induced TNF Release

Monocytes ($1 \times 10^6$ ml$^{-1}$) were stimulated with LPS (2 µg ml$^{-1}$) and coincubated with the compounds at different concentrations ($10^{-4}$ to 10 μg $ml^{-1}$). Compounds were dissolved in DMSO/medium (2% v/v). The cells were incubated in RPMI-1640 medium glutamine/FCS supplemented and at 37° C. in a humidified atmosphere with 5% $CO_2$. After 18 to 24 hours TNF was determined in the supernatants by an human TNF specific ELISA (medgenix). Controls were nonstimulated and LPS stimulated monocytes without compounds.

9. Endotoxin Induced Shock Lethality in Mice

B6D2F1 mice (n=10) were sensitized with galactosamine (600 mg/kg), and shock and lethality were triggered by LPS (0.01 μg/mouse). The compounds were administered intravenously 1 hour prior LPS. Controls were LPS challenged mice without compound. Mice were dying 8 to 24 hours post LPS challenge.

The galactosamine/LPS mediated mortality was reduced. Stimulation of Human Monocytes and Determination of Cytokine Levels Human monocytes ($2\times10^5$ in 1 ml) were stimulated with 100 ng/ml LPS, 0.8 mg/ml zymC3b or 10 ng/ml IL-1β in the presence of test compounds. The final DMSO concentration was maintained at 0.1% v/v. Cells were incubated overnight in a humidified atmosphere of 5% $CO_2$ at 37° C. Supernatants were harvested and stored at −70° C. The TNFα concentration was measured by ELISA using the A6 anti-TNF monoclonal antibody (Miles) as the primary antibody. The secondary antibody was the polyclonal anti-TNFα antibody IP300 (Genzyme) and the detection antibody was a polyclonal anti-rabbit IgG alkaline phosphatase conjugate (Sigma). IL-10 was determined by ELISA (Biosource).

TABLE A

| Example No. | $IC_{50}$ $O_2^-$ [μM] | $IC_{50}$ PDE IV [μM] |
|---|---|---|
| 13 | 0.065 | 0.021 |
| 21 | 0.02 | 0.04 |
| 24 | 0.06 | 0.13 |
| 36 | 0.007 | 0.001 |
| 46 | 0.035 | 0.006 |
| 47 | 0.02 | 0.033 |
| 49 | 0.001 | 0.001 |

The new active compounds can be converted in a known manner into the customary formulations, such as tablets, coated tablets, pills, granules, aerosols, syrups, emulsions, suspensions and solutions, using inert, nontoxic, pharmaceutically suitable excipients or solvents. In this connection, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, in the case of the use of water as a diluent, organic solvents can be used as auxiliary solvents if appropriate.

Administration is carried out in a customary manner, preferably orally or parenterally.

In the case of parenteral administration, solutions of the active compound can be employed using suitable liquid vehicles.

In general, it has proved advantageous on intravenous administration to administer amounts from about 0.001 to 10 mg/kg, preferably about 0.01 to 5 mg/kg of body weight to achieve effective results, and on oral administration the dosage is about 0.01 to 25 mg/kg, preferably 0.1 to 10 mg/kg of body weight.

In spite of this, it may be necessary to depart from the amounts mentioned, in particular depending on the body weight or the type of application route, on individual behaviour towards the medicament, the manner of its formulation and the time or interval at which administration takes place. Thus, in some cases it may be sufficient to manage with less than the abovementioned minimum amount, while in other cases the upper limit mentioned must be exceeded. In the case of administration of relatively large amounts, it is advisable to divide these into several individual doses over the course of the day. Solvents

| | | |
|---|---|---|
| a = | dichloromethane/methanol | 15:1 (v/v) |
| b = | dichloromethane/methanol | 20:1 |
| c = | dichloromethane/methanol | 50:1 |
| d = | dichloromethane/methanol | 40:1 |
| e = | ethylacetate/cyclohexane | 5:1 |
| f = | chloroform/methanol | 10:1 |
| g = | dichloromethane/methanol | 10:1 |
| h = | dichloromethane/methanol | 30:1 |
| i = | chloroform/methanol | 30:1 |
| j = | chloroform/methanol/water/acetic acid | 70:30:5:5 |
| k = | dichloromethane/methanol/formic acid | 9:1:0.1 |

STARTING COMPOUNDS

EXAMPLE I

4-Benzyloxy-2-hydroxybenzaldehyde

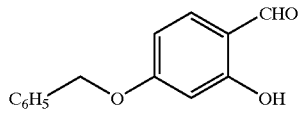

13.8 g (0.1 mol) 2,4-dihydroxybenzaldehyde are dissolved in 150 ml acetone, 17.1 g (0.1 mol) benzylbromide and 13.8 g (0.1 mol) potassium carbonate are added, and the mixture is stirred at room temperature for 3 d. After filtration, the solvent is removed in vacuo and the residual crude product further purified by column chromatography on silica gel using dichloromethane as eluent.

Yield: 9.2 g (40%); m.p.: 81–82° C. $^1$H-NMR ($CDCl_3$, 400 MHz): δ=5.11 (s, 2H; $CH_2$): 6.51 (d, 1H, Ar—H); 6.61 (dd, 1H, Ar—H); 7.32–7.45 (m, 6H, Ar—H); 9.82 (s, 1H, CHO); 11.60 (s, 1H, OH) ppm.

EXAMPLE II

4-Benzyloxy-2-hydroxybenzonitrile

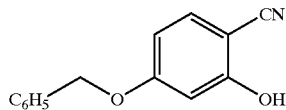

25.0 g (0.11 mol) of the compound of example I, 8.67 g (0.13 mol) hydroxylamine hydrochloride and 15.0 g (0.22 mol) sodium formate are dissolved in 170 ml formic acid, and the solution stirred under reflux for 1–3 h. The reaction mixture is cooled to room temperature, poured into ice/water and extracted with dichloromethane. The organic layer is dried ($Na_2SO_4$), the solvent removed in vacuo and the residue trituated with dichloromethane. Alternatively, the precipitate which is formed after dilution with ice/water is filtered off and dried in a desiccator in the presence of phosphorus pentoxide. The crude product is crystallized from dichloromethane/cyclohexane.

Yield: 15.0 g (61%); m.p.: 135–136° C.; $^1$H-NMR (400 MHz, DMSO-d$_6$): δ=5.13 (s, 2H, CH$_2$); 6.58 (d, 1H, Ar—H); 6.60 (dd, 1H, Ar—H); 7.32–7.46 (m, 5H, Ar—H); 7.50 (d, 1H, Ar—H); 11.10 (br.s, 1H, OH) ppm.

EXAMPLE III

ω-Bromo-2,4-dichloroacetophenone

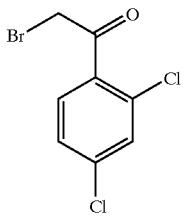

To a solution of 155.2 g (788 mmol) 2,4-dichloroacetophenone in 450 ml glacial acetic acid are added 40.4 ml (788 mmol) bromine at 50° C. After 1 h at 50° C., further 4 ml (78.8 mmol) bromine are added and the mixture is stirred for an additional hour. The solution is cooled to room temperature, concentrated to half of its volume and diluted with 800 ml water. The mixture is neutralized with solid sodium carbonate and extracted three times with ethyl acetate. The organic layer is dried (Na$_2$SO$_4$), the solvent removed in vacuo, finally under high vacuum. The crude product is used directly without further purification for the following reaction and stored in the meantime at −20° C.

Yield: 211.4 g (quant.); yellow oil.

EXAMPLE IV

3-Amino-2-(2,4-dichlorobenzoyl)6-benzyloxy-benzofuran

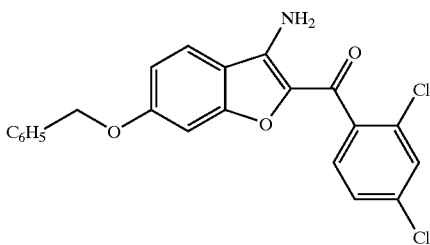

Single step procedure: 10.0 g (44.0 mmol) of the compound of example II are dissolved in 200 ml ethanol, and 5.98 g (88.0 mmol) sodium ethylate and 15.4 g (48.0 mmol) of the compound of example III are added. The mixture is stirred under reflux for 4 d. During this time further 12.0 g sodium ethylate and 7.7 g of the compound of example III are added. The solvent is removed in vacuo and the residue is purified by column chromatography on silica gel (eluent: 1. dichloromethane, 2. dichloromethane/methanol 98:2).

Yield: 8.1 g (44%); m.p.: 158° C.; NMR-data see below.

Example IVa

Two step procedure:
a) ω-[(5-Benzyloxy-2-cyano)phenoxy]-2,4-dichloroacetophenone:

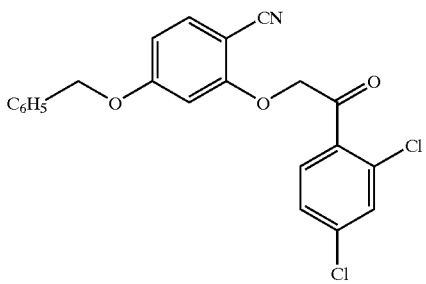

To a mixture of 26.6 g (118 mmol) of the compound of example II and 48.85 g (354 mmol) powdered potassium carbonate in 800 ml acetone are added 34.8 g (130 ml) of the compound of example III under reflux. After a further 1–2 h under reflux, the mixture is filtered, the solvent evaporated in vacuo and the residue triturated using dichloromethane (1st crop of product) and dichloromethane/cyclohexane (4:1) (2nd crop of product).

Yield: 26.2 g (54%).

b) 3-Amino-2-(2,4-dichlorobenzoyl)-6-benzyloxy-benzofuran

To a solution of 37.5 g (91 mmol) of the compound of example IVa a) in 550 ml ethanol, three pellets of sodium hydroxide are added and the mixture is stirred at 50° C. for 30 min. After cooling to room temperature, the mixture is filtered off (1st crop of product) and the filtrate is diluted with 300 ml of water. Most of the ethanol is removed in vacuo and the formed precipitate is filtered (2nd crop of product).

Yield: 36.7 g (98%); $^1$H-NMR (DMSO-d$_6$, 400 MHz): δ=5.14 (s, 2H, CH$_2$): 6.97 (dd, 1H, Ar—H); 7.10 (d, 1H, Ar—H); 7.31–7.47 (m, 5H, Ar—H) 7,53 (br.s, 2H, NH$_2$); 7.57 (s, 2H, Ar—H); 7.75 (s, 1H, Ar—H); 7.93 (d, 1H, Ar—H); ppm. Ms(EI):411 (M$^+$).

EXAMPLE V

N-[2-(2,4-Dichlorobenzoyl)-6-benzyloxy-benzofuran-3-yl]urea

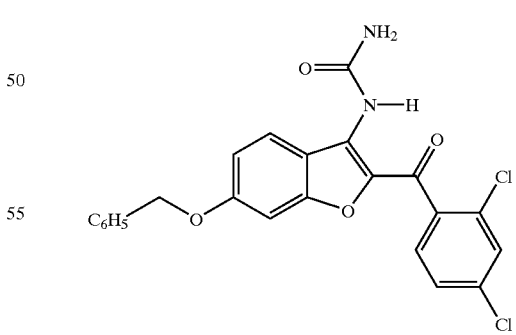

30.9 g (75 mmol) of the compound of example IV or IVa are dissolved in 750 ml dichloromethane and cooled to 0°C. 11.6 g (82 mmol) chlorosulfonyl isocyanate in dichloromethane are added and the mixture is stirred at 0° C. for 30 min and at room temperature for 3 h. The solvent is removed in vacuo, the residue suspended in water and stirred vigorously for 3 h at 60° C. After cooling to r.t. the suspension is filtered, the crude product dried in a desiccator in the presence of phosphorus pentoxide and triturated with diisopropylether at 40° C.;.

Yield: 33.7 g (98%); m.p.: 192–193° C.; $^1$H-NMR (DMSO-d$_6$, 400 MHz): δ=5.18 (s, 2H, CH$_2$); 7.00 (dd, 1H, Ar—H): 7.05 (br.s, 2H, NH$_2$): 7.20 (d, 1H, Ar—H); 7.30–7.47 (m, 5H, Ar—H); 7.61 (dd, 1H, Ar—H); 7.68; (d, 1H, Ar—H); 7.82 (d, 1H, Ar—H); 8.37 (d, 1H, Ar—H); 9.71 (s, 1H, NH) ppm. MS (FAB): 455 (M+H)$^+$.

The examples shown in Table B are prepared in analogy to the procedure for the compound of example V

TABLE B structure

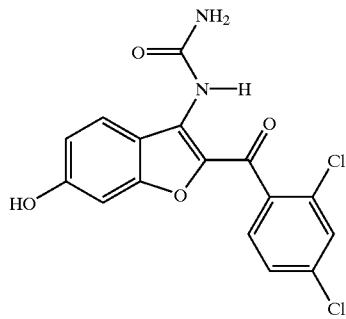

| Ex.-No. | R$^I$ | R$^{II}$ | R$^{III}$ | R$^{IV}$ | Yield (% of theory) | R$_f$* |
|---|---|---|---|---|---|---|
| Va | OCH$_3$ | H | OCH$_3$ | H | 69 | 0.30$^{b)}$ |
| Vb | F | H | F | H | 82 | 0.27$^{d)}$ |
| Vc | Cl | H | H | H | 90 | 0.18$^{c)}$ |
| Vd | H | H | Cl | H | 48 | 0.51$^{b)}$ |
| Ve | Cl | H | H | Cl | 92 | 0.47$^{b)}$ |
| Vf | CH$_3$ | H | CH$_3$ | H | 57 | 0.45$^{b)}$ |

EXAMPLE VI

N-[2-(2,4-Dichlorobenzoyl)-6-hydroxy-benzofuran-3-yl]urea

To a solution of 5.0 g of the compound of example V in 100 ml THF are added 250 mg 10% palladium on activated charcoal, and the mixture is hydrogenated at atmospheric pressure and room temperature for 1–3 d. If neccessary, further 125 mg 10% Pd/C are added and the hydrogenation is continued for 24 h. The mixtures is filtered through celite and the solvent is removed in vacuo to about ⅓ of the original volume. Dichloromethane is added, the mixture is stirred at 0° C. and the formed precipitate is filtered off.

Yield: 4.0 g (quant.); m.p.: 230–231° C.; $^1$H-NMR (DMSO-d$_6$, 400 MHz): δ=6.73 (d, 1H, Ar—H); 6.80 (dd, 1H, Ar—H); 7.03 (br.s, 2H, NH$_2$): 7.60 (dd, 1H, Ar—H); 7.65 (d, 1H, Ar—H); 7.80 (s, 1H, Ar—H); 8.30 (d, 1H, Ar—H); 9.72 (s, 1H, NH); 10.40 (br.s, 1H, OH) ppm. MS (EI): 364 (M$^+$).

Compounds shown in table I and II are prepared in analogy to example VI, characterized in that the corresponding 6-benzyloxy benzofurane is dissolved in tetrahydrofurane and hydrogenated under atmospheric pressure in the presence of 10% palladium on charcoal for 1–3 days. If neccessary, further 10% Pd/C is added and hydrogenation is continued for 24 h. The mixture is filtered and the filtrate concentrated to about one third of the original volume until precipitation of product starts. An equal volume of dichloromethane is added, the mixture is stirred for 30 minutes, and the product is isolated by suction filtration. The filtrate is concentrated, re-dissolved in tetrahydrofurane, and dichloromethane added again at 0° C. to yield a second crop of product.

TABLE I

| Ex.-No. | R$^I$ | R$^{II}$ | R$^{III}$ | R$^{IV}$ | Yield (% of th.) | R$_f$* |
|---|---|---|---|---|---|---|
| VII | F | H | F | H | 90 | 0.76$^{j)}$ |
| VIII | H | H | Cl | H | 40 | 0.38$^{a)}$ |
| IX | OCH$_3$ | H | OCH$_3$ | H | 88 | 0.38$^{a)}$ |
| X | Cl | H | H | H | 91 | 0.36$^{a)}$ |
| XI | Cl | H | H | Cl | 91 | 0.31$^{b)}$ |
| XII | CH$_3$ | H | CH$_3$ | H | 58 | 0.26$^{b)}$ |

TABLE II

| Ex.-No. | Structure |
|---|---|
| XIII | 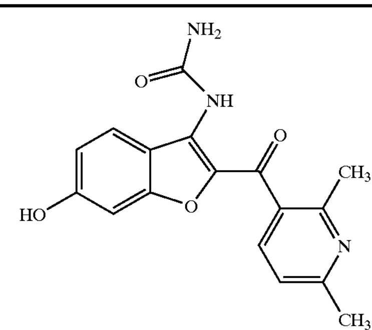 |

PREPARATION EXAMPLES

General Procedure for the Synthesis of the Benzofuranyl Sulfonates

The corresponding 6-hydroxybenzofuran component is dissolved in dry tetrahydrofurane (with addition of dry N,N-dimethylformamide if neccessary), and 1.5–2 mol equivalents triethylamine, 1.25–1.75 mol equivalents of the corresponding sulfonyl chloride and a catalytic amount of 4-dimethylaminopyridine are added successively at 0° C. The reaction mixture is stirred at room temperature overnight (or.for several days if necessary) and concentrated. The residue is taken up in dichloromethane, chloroform or ethyl acetate, and repeatedly washed with water. The organic layer is dried over sodium sulfate and concentrated. The crude product is purified by trituration with a suitable solvent or by column chromatography over silica gel.

In analogy to the general procedure the following examples shown in table 1 are prepared:

TABLE 1

| Ex. No. | D | $R^I$ | $R^{II}$ | $R^{III}$ | $R^{IV}$ | Yield (% of th.) | $R_f$* |
|---|---|---|---|---|---|---|---|
| 1 | 4-methylphenyl | Cl | H | Cl | H | 75.9 | 0.52[a)] |
| 2 | 3-(morpholin-4-yl)propyl | Cl | H | Cl | H | 67 | 0.34[b)] |
| 3 | (E)-2-phenylethenyl | Cl | H | Cl | H | 32.7 | 0.25[c)] |
| 4 | 4-acetamidophenyl | Cl | H | Cl | H | 57.4 | 0.26[b)] |
| 5 | 3-(phthalimido)propyl | Cl | H | Cl | H | 80.4 | 0.49[b)] |
| 6 | 4-chlorobutyl | Cl | H | Cl | H | 89.7 | 0.33[d)] |
| 7 | 2-phenylethyl | Cl | H | Cl | H | 83 | 0.52[b)] |
| 8 | 2-acetamido-4,5-dimethylthiazol-yl | Cl | H | Cl | H | 50.4 | 0.39[a)] |

TABLE 1-continued

| Ex. No. | D | R^I | R^II | R^III | R^IV | Yield (% of th.) | R_f* |
|---|---|---|---|---|---|---|---|
| 9 | 1,4-dimethylimidazol-2-yl | Cl | H | Cl | H | 68 | 0.43[a] |
| 10 | 5-methyl-2-(phenylsulfonyl)thiophen-yl | Cl | H | Cl | H | 70 | 0.61[a] |
| 11 | 3,4,5-trimethylisoxazol-yl | Cl | H | Cl | H | 84.5 | 0.48[b] |
| 12 | 4-acetamidophenyl-methyl | F | H | F | H | 88.5 | 0.21[e] |
| 13 | 4-acetamidophenyl-methyl | H | H | Cl | H | 38.1 | 0.41[f] |
| 14 | 4-acetamidophenyl-methyl | OCH_3 | H | OCH_3 | H | 33 | 0.54[g] |
| 15 | 4-acetamidophenyl-methyl | Cl | H | H | H | 72.5 | 0.21[e] |
| 16 | 3,4,5-trimethylisoxazol-yl | OCH_3 | H | OCH_3 | H | 65.4 | 0.48[b] |

TABLE 1-continued

| Ex. No. | D | R^I | R^II | R^III | R^IV | Yield (% of th.) | R_f* |
|---|---|---|---|---|---|---|---|
| 17 | 3,4-dimethyl-5-methylisoxazol-4-yl | F | H | F | H | 81.4 | 0.39[b] |
| 18 | 3,4-dimethyl-5-methylisoxazol-4-yl | Cl | H | H | H | 76 | 0.45[b] |
| 19 | 3,4-dimethyl-5-methylisoxazol-4-yl | H | H | Cl | H | 73.8 | 0.43[b] |
| 20 | 1,4-dimethylimidazol-2-yl | OCH$_3$ | H | OCH$_3$ | H | 79 | 0.39[a] |
| 21 | 5-(pyridin-2-yl)thiophen-2-yl | Cl | H | Cl | H | 77 | 0.49[b] |
| 22 | 5-chloro-1,3-dimethyl-4-methylpyrazol-4-yl | Cl | H | Cl | H | 67 | 0.39[b] |
| 23 | 5-chloro-1,3-dimethyl-4-methylpyrazol-4-yl | OCH$_3$ | H | OCH$_3$ | H | 60.4 | 0.28[a] |
| 24 | 5-chloro-1,3-dimethyl-4-methylpyrazol-4-yl | F | H | F | H | 62.8 | 0.45[a] |

TABLE 1-continued

[Structure: benzofuran core with 3-NH-C(O)-NH₂ (urea), 2-position benzoyl group with substituents R^I, R^II, R^III, R^IV on phenyl ring, and 6-O-SO₂-D sulfonate]

| Ex. No. | D | $R^I$ | $R^{II}$ | $R^{III}$ | $R^{IV}$ | Yield (% of th.) | $R_f$* |
|---|---|---|---|---|---|---|---|
| 25 | 5-chloro-1,3-dimethyl-pyrazol-4-yl | Cl | H | H | H | 68.7 | 0.54[a] |
| 26 | 5-chloro-1,3-dimethyl-pyrazol-4-yl | H | H | Cl | H | 63.4 | 0.53[a] |
| 27 | 1,4-dimethyl-imidazol-5-yl | F | H | F | H | 88 | 0.28[a] |
| 28 | 1,4-dimethyl-imidazol-5-yl | Cl | H | H | H | 53.4 | 0.32[a] |
| 29 | 1,4-dimethyl-imidazol-5-yl | H | H | Cl | H | 75 | 0.35[a] |
| 30 | 3-methyl-2-(methoxycarbonyl)-thiophen-... | Cl | H | Cl | H | 76.6 | 0.59[a] |
| 31 | 1,5-dimethyl-imidazol-4-yl | Cl | H | H | Cl | 90 | 0.41[a] |

TABLE 1-continued

| Ex. No. | D | R^I | R^II | R^III | R^IV | Yield (% of th.) | R_f* |
|---|---|---|---|---|---|---|---|
| 32 | 5-chloro-1,3-dimethyl-pyrazol-4-yl | Cl | H | H | Cl | 85.2 | 0.57[a] |
| 33 | 3,4-dimethyl-5-methyl-isoxazolyl | Cl | H | H | Cl | 81.2 | 0.44[b] |
| 34 | N-(4-methylphenyl)acetamido | Cl | H | H | Cl | 84.4 | 0.37[a] |
| 35 | 5-methyl-2-(pyridin-2-yl)thiophen-yl | Cl | H | H | Cl | 74 | 0.58[a] |
| 36 | 1,4-dimethyl-imidazol-5-yl | CH$_3$ | H | CH$_3$ | H | 70 | 0.46[f] |
| 37 | 3,4-dimethyl-5-methyl-isoxazolyl | CH$_3$ | H | CH$_3$ | H | 72 | 0.48[a] |

TABLE 1-continued
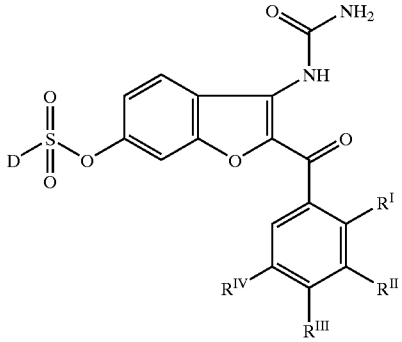
| Ex. No. | D | $R^I$ | $R^{II}$ | $R^{III}$ | $R^{IV}$ | Yield (% of th.) | $R_f$* |
|---|---|---|---|---|---|---|---|
| 38 | 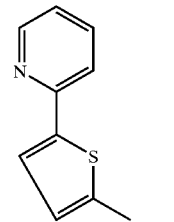 | $CH_3$ | H | $CH_3$ | H | 89 | 0.42[b)] |
| 39 | 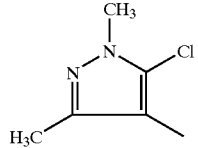 | $CH_3$ | H | $CH_3$ | H | 81 | 0.34[a)] |
| 40 | 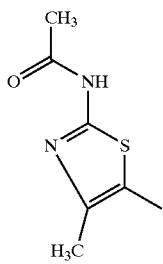 | $CH_3$ | H | $CH_3$ | H | 82.2 | 0.43[a)] |
| 41 | 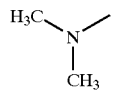 | $CH_3$ | H | $CH_3$ | H | 80 | 0.45[a)] |
| 42 | 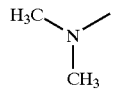 | Cl | H | Cl | H | 63 | 0.27[c)] |
| 43 | 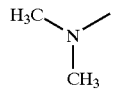 | $CH_3$ | H | $CH_3$ | H | 57 | 0.24[c)] |
| 44 | 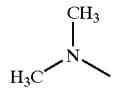 | $OCH_3$ | H | $OCH_3$ | H | 75 | 0.48[a)] |

TABLE 1-continued
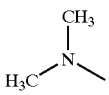
| Ex. No. | D | R<sup>I</sup> | R<sup>II</sup> | R<sup>III</sup> | R<sup>IV</sup> | Yield (% of th.) | R<sub>f</sub>* |
|---|---|---|---|---|---|---|---|
| 45 | 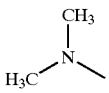 | F | H | F | H | 47 | 0.33<sup>h)</sup> |
| 46 | 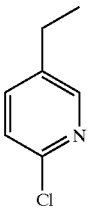 | Cl | H | H | Cl | 60.5 | 0.42<sup>b)</sup> |
| 47 | 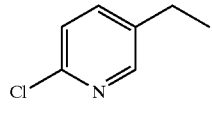 | Cl | H | Cl | H | 31 | 0.39<sup>b)</sup> |
| 48 | 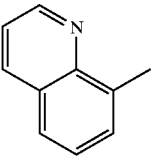 | Cl | H | H | Cl | 50.5 | 0.23<sup>b)</sup> |
| 49 | 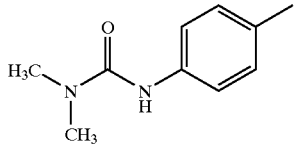 | Cl | H | Cl | H | 77 | 0.48<sup>a)</sup> |
| 50 | 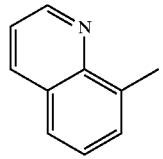 | Cl | H | Cl | H | 81 | 0.42<sup>a)</sup> |
| 51 |  | Cl | H | H | Cl | 67.3 | 0.54<sup>a)</sup> |

TABLE 1-continued
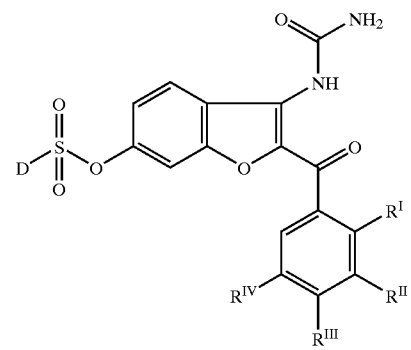
| Ex. No. | D | $R^I$ | $R^{II}$ | $R^{III}$ | $R^{IV}$ | Yield (% of th.) | $R_f$* |
|---|---|---|---|---|---|---|---|
| 52 | H₃C−N(CH₃)−C(O)−NH−C₆H₄−CH₃− | Cl | H | H | Cl | 93 | 0.41[a] |
| 53 | H₃CO₂C−NH−C₆H₄−CH₃− | Cl | H | Cl | H | 3.5 | 0.30[i] |
| 54 | H₂N−SO₂−C₆H₄−CH₃− | Cl | H | Cl | H | 17.4 | 0.22[f] |
| 55 | H₂N−SO₂−C₆H₄−CH₃− | Cl | H | H | Cl | 1.8 | 0.47[f] |
| 56 | H₃CO₂C−NH−C₆H₄−CH₃− | Cl | H | H | Cl | 4.1 | 0.28[i] |
| 57 | (H₃C)₂N−SO₂−NH−C₆H₄−CH₃− | Cl | H | Cl | H | 25.3 | 0.24[i] |
| 58 | morpholine-N-CH₂− | Cl | H | Cl | H | 16 | 0.39[i] |
| 59 | morpholine-N-CH₂− | Cl | H | H | Cl | 20.8 | 0.38[i] |
| 60 | thiophene-CH₂− | Cl | H | H | Cl | | |

TABLE 2

| Ex.-No. | Structure | Yield (% of theory) | $R_f$* |
|---|---|---|---|
| 61 | 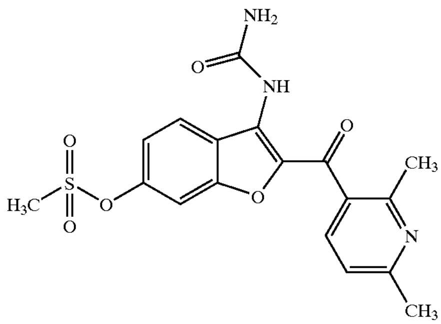 | 49.6 | 0.54[g] |
| 62 | 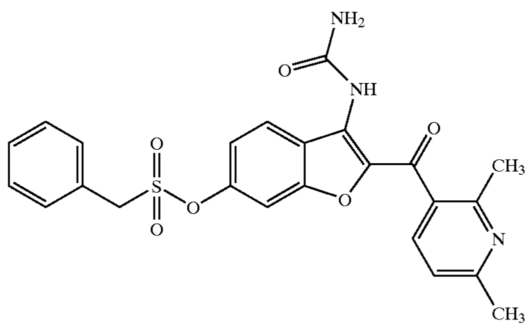 | 7.1 | 0.28[g] |
| 63 | 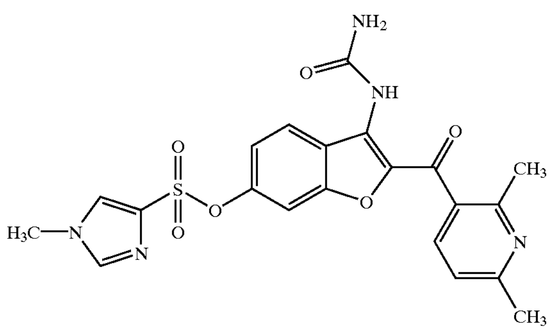 | 72.5 | 0.45[g] |
| 64 | 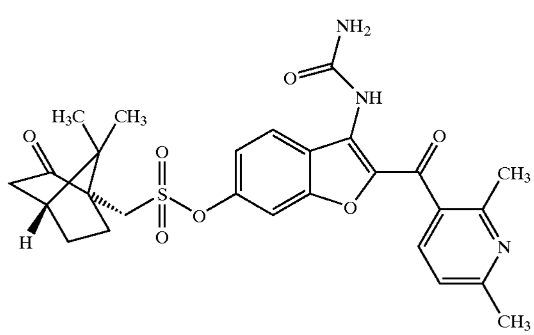 | 21.6 | 0.49[g] |

TABLE 2-continued
| Ex.-No. | Structure | Yield (% of theory) | $R_f$* |
|---|---|---|---|
| 65 | 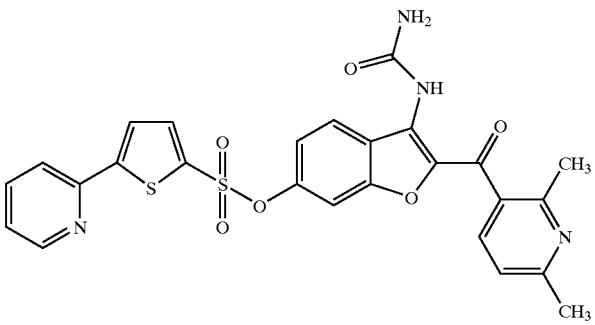 | 21.3 | 0.46[g] |
| 66 | 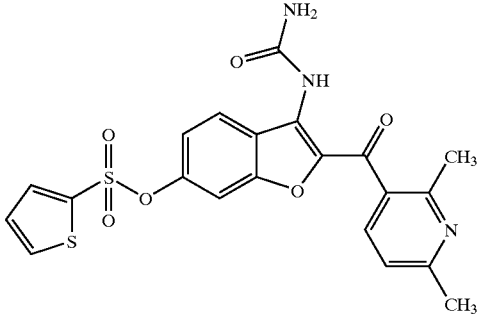 | 63.1 | 0.51[g] |
| 67 | 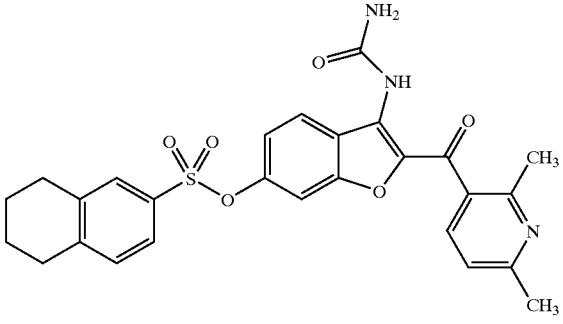 | 38.7 | 0.48[g] |
| 68 | 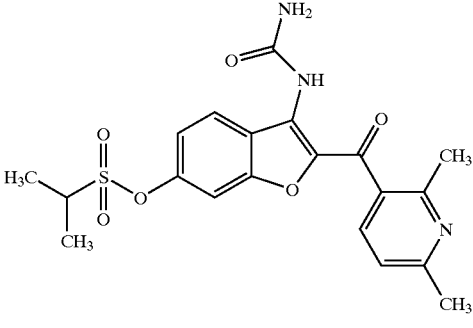 | 37.1 | 0.25[b] |

TABLE 2-continued

| Ex.-No. | Structure | Yield (% of theory) | $R_f$* |
|---|---|---|---|
| 69 | 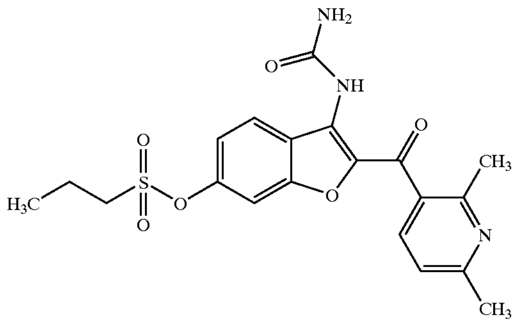 | 57.9 | 0.27[b)] |
| 70 | 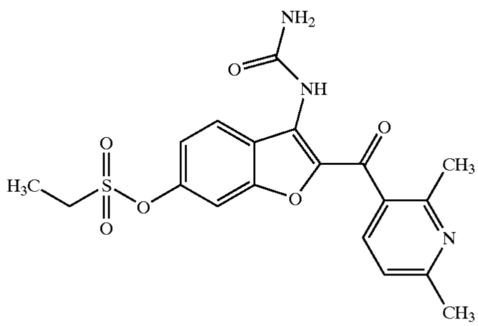 | 21.6 | 0.25[b)] |
| 71 | 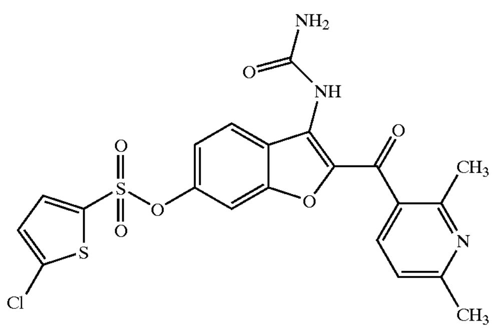 | 77.2 | 0.29[b)] |

We claim:

1. Benzofuranylsulfonates of the general formula (I)

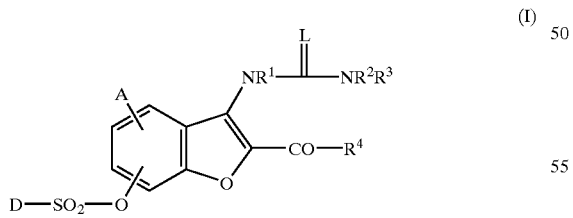

in which

A represents hydrogen, straight-chain or branched acyl or alkoxycarbonyl, each having up to 6 carbon atoms, halogen, carboxyl, cyano, nitro, hydroxyl, trifluoromethyl or trifluoromethoxy, or straight-chain or branched alkyl having up to 6 carbon atoms, which is optionally substituted by carboxyl, alkoxy or alkoxycarbonyl each having up to 4 carbon atoms, phenoxy or benzoyl, $R^1$ represents hydrogen, straight-chain or branched alkyl having up to 4 carbon atoms, an amino protecting group or a group of the formula —CO—$R^5$ in which $R^5$ denotes straight chain or branched alkoxy having up to 4 carbon atoms, $R^2$ and $R^3$ are identical or different and represent hydrogen, cycloalkyl having up to 6 carbon atoms, straight chain or branched alkyl, alkoxycarbonyl or alkenyl each having up to 8 carbon atoms, or $R^2$ and $R^3$ together with the nitrogen atom form a 5- to 7-membered saturated heterocycle optionally having a further O atom, $R^4$ represents aryl having 6 to 10 carbon atoms or represents a 5 to 7 membered, aromatic, saturated or unsaturated heterocycle, which can contain up to 3 heteroatoms selected from oxygen, sulphur and nitrogen atoms, or a residue of a formula —$NR^6$, wherein $R^6$ denotes hydrogen or straight-chain or branched alkyl or alkoxycarbonyl each having up to 6 carbon atoms, and to which further a benzene ring can be fused and wherein aryl and the heterocycle are optionally monosubstituted to trisubstituted by identical or different substituents from the series hydroxyl, halogen, nitro, 1H-tetrazolyl, pyridyl, trifluoromethyl, trifluromethoxy, difluoromethyl, difluoromethoxy, cyano, carboxy, straight-chain or branched alkoxy, alkoxycarbonyl or acyl each having up to 6 carbon atoms or by straight-chain or branched alkyl having up to 5 carbon atoms, which is optionally substituted by carboxyl or straight-chain or branched alkoxycarbonyl having up to 4 carbon atoms or by a group of formula —NR$^7$R$^8$, —SR$^9$, —(NH)$_a$—SO$_2$R$^{10}$ or —O—SO$_2$R$^{11}$,
in which
R$^7$ and R$^8$ are identical or different and denote hydrogen or a straight-chain or branched alkyl having up to 4 carbon atoms,
or
R$^7$ denotes hydrogen
and
R$^8$ denotes straight-chain or branched acyl having up to 6 carbon atoms
R$^9$ denotes hydrogen or straight-chain or branched alkyl having up to 4 carbon atoms,
a denotes a number 0 or 1,
R$^{10}$ and R$^{11}$ are identical or different and represent straight-chain or branched alkyl having up to 6 carbon atoms, benzyl or phenyl, which are optionally substituted by trifluoromethyl, halogen or straight-chain or branched alkyl having up to 4 carbon atoms,
L represents an oxygen or sulfur atom,
D represents a residue of a formula

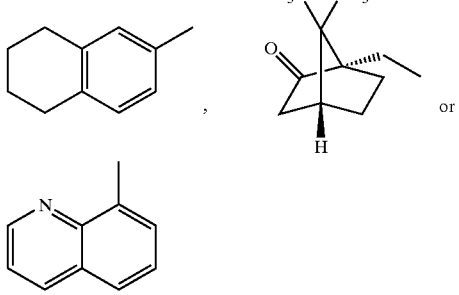

or aryl having 6 to 10 carbon atoms or a 5 to 7-membered aromatic, saturated or unsaturated heterocycle having up to 3 heteroatoms from the series N, S and O and to which a phenyl ring can be fused, wherein all abovementioned residues and ring systems are optionally monosubstituted to trisubstituted by at least one substituent selected from halogen, carboxyl, straight-chain or branched alkyl or alkoxycarbonyl each having up to 6 carbon atoms, pyridyl, and groups having the formulae —NR$^{12}$—E—R$^{13}$, —NR$^{14}$—CO—NR$^{15}$R$^{16}$, —NR$^{17}$—SO$_2$—NR$^{18}$R$^{19}$, —SO$_2$R$^{20}$ and —(SO$_2$)$_b$—NR$^{21}$R$^{22}$,
wherein
b denotes a number 0 or 1,
E denotes a residue of formula SO$_2$ or CO,
R$^{12}$, R$^{14}$, R$^{15}$, R$^{16}$, R$^{17}$, R$^{18}$, R$^{19}$, R$^{21}$ and R$^{22}$ are identical or different and denote hydrogen, phenyl or straight-chain or branched alkyl having up to 6 carbon atoms, R$^{13}$ denotes straight-chain or branched alkyl or alkoxy each having up to 6 carbon atoms,
R$^{20}$ denotes benzyl, phenyl, pyridyl or straight-chain or branched alkyl having up to 6 carbon atoms,
or
D represents straight-chain or branched alkyl or alkenyl having up to 8 carbon atoms, which are monosubstituted to trisubstituted by at least one substituent selected from halogen, aryl having 6 to 10 carbon atoms, a 5 to 7-membered saturated or unsaturated heterocycle having up to 3 heteroatoms from the series N, S and O and to which a phenyl ring can be fused, a group of formula —NR$^{23}$R$^{24}$,
and

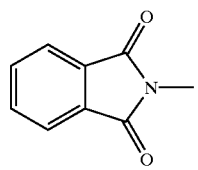

wherein
R$^{23}$ and R$^{24}$ have the abovementioned meaning of R$^{15}$ and R$^{16}$ and are identical or different.
wherein the abovementioned ring systems are optionally substituted by halogen,
and in the case that
R$^4$ does not represent phenyl or substituted phenyl,
D in addition can represent benzyl or straight-chain or branched alkyl having up to 5 carbon atoms,
or
D optionally represents a residue of a formula —NR$^{25}$R$^{26}$
wherein
R$^{25}$ and R$^{26}$ have the abovementioned meaning of R$^{21}$ and R$^{22}$ and are identical or different,
and salts thereof.
2. Compounds according to claim 1, in which
A represents hydrogen, halogen, carboxyl, cyano, nitro, hydroxyl, trifluoromethyl, trifluoromethoxy or alkoxy having up to 4 carbon atoms,
R$^1$ represents hydrogen, straight-chain or branched alkyl having up to 4 carbon atoms or a group of the formula —CO—R$^5$
in which
R$^5$ denotes straight chain or branched alkoxy having up to 4 carbon atoms,
R$^2$ and R$^3$ are identical and represent hydrogen, cyclobutyl, cyclopentyl, cyclohexyl or straight-chain or branched alkyl, alkoxycarbonyl or alkenyl each having up to 4 carbon atoms,
or
R$^2$ and R$^3$ together with the nitrogen atom form a pyrrolidinyl-, piperidinyl- or morpholinyl-ring,
and
R$^4$ represents phenyl, pyridyl or thienyl, wherein all rings are optionally monosubstituted to trisubstituted by identical or different substituents selected from hydroxyl, fluorine, chlorine, bromine, nitro, carboxy, straight-chain or branched alkoxy, alkoxycarbonyl or acyl each having up to 3 carbon atoms, and straight-chain or branched alkyl having up to 3 carbon atoms, which is optionally substituted by carboxyl or straight-chain or branched alkoxycarbonyl having up to 3 carbon atoms, L represents an oxygen or sulfur atom, D represents a residue of a formula

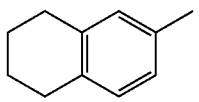 , 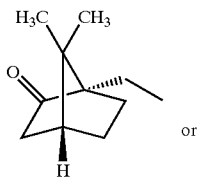 or

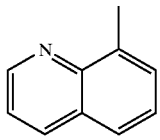

or phenyl, pyridyl, thienyl, furyl, pyrazolyl, oxazolyl, isoxazolyl, thiazolyl, imidazolyl, morpholinyl, piperidinyl, pyrrolidinyl or piperazinyl, wherein all abovementioned residues and ring systems are optionally monosubstituted to trisubstiuted by at least one subsituent selected from halogen, carboxyl, straight-chain or branched alkyl or alkoxycarbonyl each having up to 4 carbon atoms, pyridyl, and groups having the formulae $—NR^{12}—E—R^{13}$, $—NR^{14}—CO—NR^{15}R^{16}$, $—NR^{17}—SO_2—NR^{18}R^{19}$, $—SO_2—R^{20}$ and $—(SO^2)_b—NR^{21}R^{22}$, wherein b denotes a number 0 or 1, E denotes a residue of formula $SO_2$ or CO, $R^{12}$, $R^{14}$, $R^{15}$, $R^{16}$, $R^{17}R^{18}$, $R^{19}$, $R^{21}$ and $R^{22}$ are identical or different and denote hydrogen, phenyl or straight-chain or branched alkyl having up to 4 carbon atoms, $R^{13}$ denotes straight-chain or branched alkyl or alkoxy each having up to 4 carbon atoms, $R^{20}$ denotes benzyl, phenyl, pyridyl, ethyl or methyl, or D represents straight-chain or branched alkyl or alkenyl having up to 6 carbon atoms, which are monosubstituted to trisubstituted by at least one substituent selected from halogen, phenyl, pyridyl, thienyl, furyl, imidazolyl, morpholinyl, piperidinyl, pyrrolidinyl, piperazinyl, a group of formula $—NR^{23}R^{24}$, and

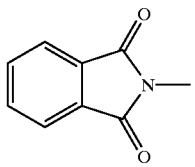

wherein $R^{23}$ and $R^{24}$ have the abovementioned meaning of $R^{15}$ and $R^{16}$ and are identical or different, wherein the above mentioned ring systems are optionally substituted by halogen, and in the case that $R^4$ does not represent phenyl or substituted phenyl, D additionally can represent benzyl or straight-chain or branched alkyl having up to 4 carbon atoms, or D optionally represents a group of formula $—NR^{25}R^{26}$ wherein $R^{25}$ and $R^{26}$ have the above mentioned meaning of $R^{21}$ and $R^{22}$ and are identical or different, and salts thereof.

3. Compounds according to claim 1 or 2, in which

A, $R^2$ and $R^3$ represent hydrogen, $R^1$ represents hydrogen or straight-chain or branched alkyl having up to 3 carbon atoms or a group of the formula $—CO—R^5$, in which $R^5$ denotes straight chain or branched alkoxy having up to 3 carbon atoms, $R^4$ represents phenyl or pyridyl, which are optionally up to twofold substituted by identical or different substituents selected from the series fluorine, chlorine, methyl and methoxy, L represents an oxygen atom, D represents a residue of a formula

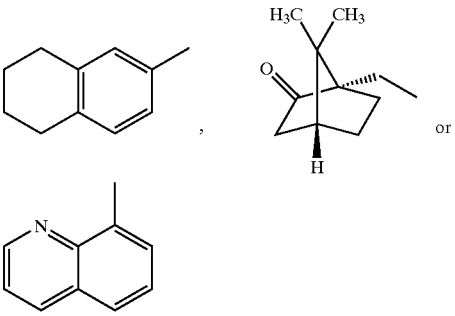

or phenyl, pyridyl, thienyl, pyrazolyl, oxazolyl, isoxazolyl, thiazolyl, imidazolyl, morpholinyl, piperidinyl, pyrrolidinyl or piperazinyl, wherein all abovementioned residues and ring systems are optionally monosubstituted to trisubstituted by at least one substituent selected from halogen, carboxyl, straight-chain or branched alkyl or alkoxycarbonyl each having up to 3 carbon atoms, pyridyl and groups having the formulae $—NR^{12}—E—R^{13}$, $—NR^{14}—CO—NR^{15}R^{16}$, $—NR^{17}—SO_2—NR^{18}R^{19}$, $—SO_2—R^{20}$ and $—(SO_2)_b—NR^{21}R^{22}$, wherein b denotes a number 0 or 1, E denotes a residue of formula $SO_2$ or CO, $R^{12}$, $R^{14}$, $R^{15}$, $R^{16}$, $R^{17}$, $R^{18}$, $R^{19}$, $R^{21}$ and $R^{22}$ are identical or different and denote hydrogen, phenyl or straight-chain or branched alkyl having up to 3 carbon atoms, $R^{13}$ denotes straight-chain or branched alkyl or alkoxy each having up to 3 carbon atoms, $R^{20}$ denotes benzyl, phenyl, or methyl, or D represents straight-chain or branched alkyl or alkenyl having up to 4 carbon atoms, which are monosubstituted to trisubstituted by at least our substituent selected from halogen, phenyl, pyridyl, thienyl, furyl, imidazolyl, morpholinyl, piperidinyl, pyrrolidinyl, piperazinyl, a group of formula —NR$^{23}$R$^{24}$ and

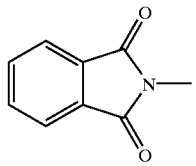

wherein
R$^{23}$ and R$^{24}$ have the abovementioned meaning of R$^{15}$ and R$^{16}$ and are identical or different,
wherein the abovementioned ring systems are optionally substituted by halogen,
and in the case that
R$^4$ does not represent phenyl or substituted phenyl,
D Additionally can represent benzyl or straight-chain or branched alkyl having up to 3 carbon atoms,
or
D optionally represents a group of formula —NR$^{25}$R$^{26}$
wherein
R$^{25}$ and R$^{26}$ have the abovementioned meaning of R$^{21}$ and R$^{22}$ and are identical of different,
and salts thereof.

4. A process for the preparation of the compounds according to claim 1, characterized in that compounds of the general formula (II)

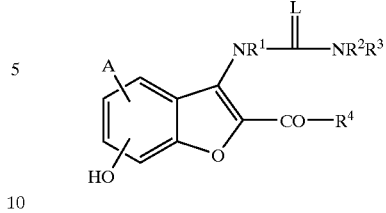

in which
A, L, R$^1$, R$^2$, R$^3$ and R$^4$ have the meanings defined in claim 1
are reacted with compounds of the general formula (III)

 (III)

in which
D has the meaning defined in claim 1,
in an inert solvent.

5. The process of claim 4 in which the reaction in said inert solvent is carried out in the presence of at least one of a) a base and b) an auxiliary.

6. A pharmaceutical composition comprising at least one Benzofuranylsulfonate according to claim 1 and a pharmacologically acceptable diluent.

7. A method of treating or preventing inflammation in a mammal comprising administering an effective amount of a compound according to claim 1.

8. The method of claim 7 wherein the inflammation is acute.

9. The method of claim 7 wherein the inflammation is chronic.

* * * * *